(12) United States Patent
Lin et al.

(10) Patent No.: US 7,544,846 B1
(45) Date of Patent: Jun. 9, 2009

(54) METHOD FOR PRODUCING 1,4-BIS(DIFLUOROMETHYL) TETRAFLUOROBENZENE

(75) Inventors: Chun-Hsu Lin, Taipei (TW);
Chac-Chou Tu, Hsinchu County (TW);
Chan-Yuan Ho, Hsinchu (TW);
Chuan-Yu Chou, Jhongli (TW);
Wei-Hsiung Ou, Longtan Township, Taoyuan County (TW); Shieh-Jun Wang, Taipei (TW)

(73) Assignees: Yuan-Shin Materials Technology Corp. (TW); Chung-Shan Institute of Science and Technology, Armaments Bureau, M.N.D. (TW)

( * ) Notice: Subject to any disclaimer, the term of this patent is extended or adjusted under 35 U.S.C. 154(b) by 0 days.

(21) Appl. No.: 12/219,789

(22) Filed: Jul. 29, 2008

(30) Foreign Application Priority Data

Dec. 28, 2007 (TW) .............................. 96150782 A

(51) Int. Cl.
*C07C 22/00* (2006.01)
*C07C 17/20* (2006.01)

(52) U.S. Cl. ....................................... 570/145; 570/170
(58) Field of Classification Search .................. 570/145, 570/170
See application file for complete search history.

(56) References Cited

OTHER PUBLICATIONS

Bailey et al., Fluorination with complex metal fluorides, (Journal of Fluorine Chemistry, 1987, 37 pages 1-14).*

* cited by examiner

*Primary Examiner*—Jafar Parsa
(74) *Attorney, Agent, or Firm*—Bacon & Thomas, PLLC

(57) ABSTRACT

A method for producing 1,4-bis(difluoromethyl)tetrafluorobenzene is disclosed, which has the following steps: (a) mixing 1,4-bis(dichloromethyl)tetrafluorobenzene, a catalyst, an aprotic polar solvent, and an alkali metal fluoride to form a reaction mixture; (b) heating the reaction mixture; and (c) purifying the resultant to obtain 1,4-bis(difluoromethyl) tetrafluorobenzene.

13 Claims, No Drawings

METHOD FOR PRODUCING 1,4-BIS(DIFLUOROMETHYL) TETRAFLUOROBENZENE

BACKGROUND OF THE INVENTION

1. Field of the Invention

The present invention relates to a method for halogen exchange reaction and, more particularly, to a method for producing 1,4-bis(difluoromethyl)tetrafluorobenzene, which is simple and highly-yielding.

2. Description of Related Art

As techniques of integrated circuits have progressed, semiconductor components are designed towards miniaturization and high speed. In order to dispose more and more components on a finite area of a chip, i.e. to upgrade integration of components on a chip, two or more metal interconnection layers are required to be transmittals for signals between components and the external environment, and accordingly there can be provided sufficient area to make interconnects. Therefore, transmittal speed between internal components and the external environment is determined by interconnect capacitance, i.e. RC delay, rather than switching speed of gates. Since using low dielectric constant materials can alleviate RC delay, much research is currently focusing on development of low dielectric constant materials.

Organic polymers containing fluorine now are widely used due to their low dielectric constant and easy to use in processes of current semiconductor techniques. In general, methods for decreasing dielectric constant of organic materials can be classified into physical and chemical methods. In the case of physical methods, the thickness of the thin film is enlarged to reduce dielectric constant. With regard to chemical methods, there are two common ways as follows. First is to raise the amount of fluorine in a molecule: fluorine atoms are introduced into a monomer of the molecule by chemical methods to raise the amount of fluorine therein, thereby increasing atomic or molecular packing density. Second is to increase free volume: atoms or molecular groups having large volume are introduced into polymer films to lower atomic or molecular packing density, resulting in a decrease in dielectric constant.

Since polymers of aromatic compounds containing fluorine generally have advantageous properties such as transparency, thermal and chemical resistance, water repellent, low dielectric constant, low reflectivity and so on, Bailey et al. (J. Fluor. Chem., 1987, 37: 1-14) discloses a method for preparing aromatic compounds having a benzene ring substituted with four fluorine atoms and a side chain also substituted with fluorine. Specifically, in this method, the benzene ring and the side chains of p-xylene are fluorinated by complex metal fluoride. The fluorination is performed as the reaction (I) listed following.

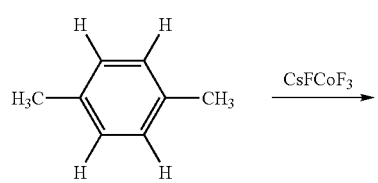

reaction (I)

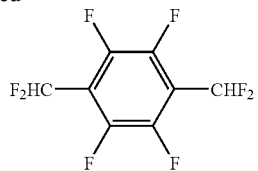

However, this method itself has shortcomings listed as follows: (1) complex metal fluorides such as CsF and $CoF_3$ are very expensive; (2) fluorination on the benzene ring and the side chain hydrogen needs to be performed under the condition of the high temperature (360° C.); (3) due to carrying out in a gas phase fluorination reaction, it needs complex equipment; and (4) varieties of excess byproducts result in difficulty of purification.

Because techniques for manufacturing integrated circuits have been upgraded progressively, there is a demand for dielectric materials to have lower and lower dielectric constants for industries, and their costs are required to be reasonable so as to enhance the competitiveness of industries. Hence, how to provide a method, which has simple reactions and can be used for quantity production, of preparing a monomer containing fluorine of a polymer with low dielectric constant has become a current issue waiting for resolution. The present invention provides a method of preparing an important precursor, 1,4-bis(difluoromethyl)tetrafluorobenzene, of 1,4-bis-(bromodifluoromethyl)tetrafluorobenzene to achieve the foregoing purposes of having simple reactions and quantity production.

SUMMARY OF THE INVENTION

In view of drawbacks described above, the present invention provides a method for producing 1,4-bis(difluoromethyl)tetrafluorobenzene. Through this method, the cost of preparing 1,4-bis(difluoromethyl)tetrafluorobenzene can be decreased and the steps thereof can be simplified. The reaction is a typical halogen substitution shown as the following reaction (II).

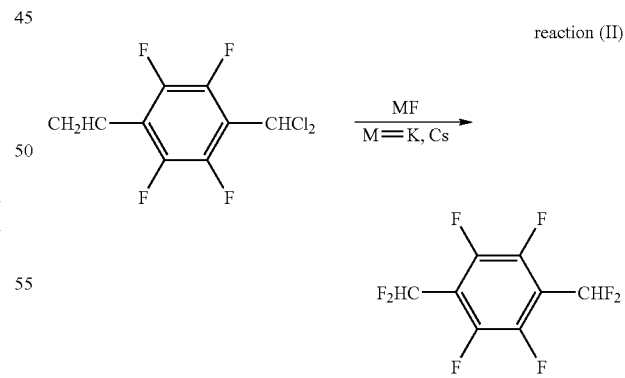

reaction (II)

The present invention provides a method for producing 1,4-bis(difluoromethyl)tetrafluorobenzene comprising the following steps:

(a) mixing 1,4-bis(dichloromethyl)tetrafluorobenzene, a catalyst, an aprotic polar solvent, and an alkali metal fluoride to form a reaction mixture;

(b) heating the reaction mixture to perform a reaction; and (c) purifying the reaction mixture to obtain 1,4-bis(difluoromethyl)tetrafluorobenzene.

In the method of the present invention, each reactant in the step (a) can be added in any order. In a preferred aspect of the present invention, the step (a) can comprise the following steps:

(a1) mixing 1,4-bis(dichloromethyl)tetrafluorobenzene, a catalyst, and an aprotic polar solvent in a reactor to form a mixture;

(a2) heating the mixture until the 1,4-bis(dichloromethyl tetrafluorobenzene dissolves; and (a3) adding an alkali metal fluoride to the mixture to form the reaction mixture.

In the method of the present invention, the reaction time of the step (b) can be in the range of from 1 to 48 hours. If the reaction time of the step (b) is less than 2 hours, the reaction yield is comparatively low. If the reaction time of the step (b) is more than 24 hours, the reaction yield does not dramatically increase. Hence, the reaction time of the step (b) is preferably in the range of from 2 to 24 hours.

In the method of the present invention, the reaction temperature of the step (b) can be in the range of from 40 to 120° C. If the reaction temperature of the step (b) is less than 50° C., the reaction becomes slow. If the reaction temperature of the step (b) is more than 110° C., gumming may easily occur in the reaction. Hence, the reaction temperature of the step (b) is preferably in the range of from 50 to 110° C.

In the method of the present invention, the catalyst can belong to phase transfer catalysts. Preferably, the catalyst can be at least one selected from the group consisting of quaternary ammonium salt, quaternary phosphonium salt, and crown ether.

In the method of the present invention, general quaternary ammonium salts all can be used. The quaternary ammonium salt has the structure represented by the following formula (III):

formula (III)

wherein X is Cl, Br, or I; $R_1$, $R_2$, $R_3$, and $R_4$ are alkyl groups, aryl groups or the combination thereof. These alkyl groups preferably are $C_1$ to $C_8$ alkyl groups. These aryl groups preferably are phenyl groups or benzyl groups. For example, $(CH_3)_4NCl$, $(C_4H_9)_4NBr$, $C_8H_{17}(CH_3)_3NBr$, $C_6H_5(CH_3)_3NCl$, etc., in which tetramethyl ammonium chloride $((CH_3)_4NCl)$ is optimum.

In the method of the present invention, general quaternary phosphonium salts all can be used. The quaternary phosphonium salt has the structure represented by the following formula (IV):

formula (IV)

wherein X is Cl, Br, or I; $R_1$, $R_2$, $R_3$, and $R_4$ are alkyl groups, aryl groups or the combination thereof. These alkyl groups preferably are $C_1$ to $C_8$ alkyl groups. These aryl groups preferably are phenyl groups or benzyl groups. For example, $(Ph)_4PBr$, $(C_4H_9)_4PBr$, $(Ph)_4PCl$ etc., in which tetraphenylphosphonium bromide $((Ph)_4PBr)$ is optimum.

In the method of the present invention, general crown ethers all can be used. For example, 12-crown-4-ether, 15-crown-5-ether, and 18-crown-6-ether, in which 18-crown-6-ether is preferable.

In the method of the present invention, general aprotic polar solvents all can be used. For example, acetonitrile, sulpholane, or N,N-dimethylformamide, in which acetonitrile is preferable.

In the method of the present invention, general alkali metal fluorides all can be used. For example, LiF, NaF, KF and CsF, in which KF or CsF is preferable.

In the method of the present invention, the mole number of the alkali metal fluoride is in the range of from 1 to 16-fold greater than that of 1,4-bis(dichloromethyl)tetrafluorobenzene, and preferably in the range of from 4- to 8-fold.

In the method of the present invention, the amount of the catalyst is in the range of from 1 to 40% wt based on 1,4-bis (dichloromethyl)tetrafluorobenzene, and preferably in the range of from 4 to 12% wt.

In the method of the present invention, purifying in the step (c) can comprise to filtrate, extract, distil, or sublimate the reaction mixture or the combination thereof, and to sublimate is optimum for purifying 1,4-bis(difluoromethyl)tetrafluorobenzene.

Other objects, advantages, and novel features of the invention will become more apparent from the following detailed description when taken in conjunction with the accompanying drawings.

DETAILED DESCRIPTION OF THE PREFERRED EMBODIMENT

Example 1

A 150-mL reacting flask was equipped with a condenser and a magnetic hotplate/stirrer. 20 g (0.063 mole) of 1,4-bis (dichloromethyl)tetrafluorobenzene (DCMTFB), 2 g of 18-crown-6-ether, and 40 mL of acetonitrile were added in the reacting flask. The oil bath was heated by the hotplate/stirrer until its temperature reached 80° C. and the abovementioned organic compounds all dissolved. Subsequently, 60 g (0.39 mole) of CsF were added into the reacting flask, and then the temperature of the oil bath rose to 100° C. After the reaction was performed for 6 hours, the product was analyzed and it was found that the conversion ratio of 1,4-bis(difluoromethyl)tetrafluorobenzene reached 92% or more. The crude product was filtrated, extracted, distilled, and sublimated to obtain 12 g of pure 1,4-bis(difluoromethyl)tetrafluorobenzene. The resultant yield was 76%.

The resultant product of the present example was verified to be 1,4-bis(difluoromethyl)tetrafluorobenzene through chemical analyses. The data of the chemical analyses are listed as follows.

(a) Mass spectrum analysis: $M^+$ 250

(b) $^1$H NMR (Tetramethylsilane, TMS):

chemical shift 6.91 ppm t, J=53.8

(c) ¹⁹F NMR (CFCl₃):
chemical shift 143.3 ppm s (aromatic F)
115.8 ppm d, J=53.8 (aliphatic F)
integration ratio (aromatic F/aliphatic F)=1/1

Example 2

A 150-mL reacting flask was equipped with a condenser and a magnetic hotplate/stirrer. 30 g (0.095 mole) of 1,4-bis (dichloromethyl)tetrafluorobenzene (DCMTFB), 45 g of KF, 45.8 g of sulpholane, and 3 g of tetraphenylphosphonium bromide were added into the reacting flask. The hotplate/stirrer was turned on, and the oil bath was set at the temperature of 125~130° C. to perform the reaction for 48 hours. In order to prevent the product from sublimation and overflowing the reacting flask, the outlet of the condenser could be plugged by a stopper. After the reaction was completed, the reaction mixture was cooled to room temperature. Subsequently, the reaction mixture was filtrated to obtain a filtered cake. The filtered cake was washed by using $CH_2Cl_2$ and distilled under reduced pressure to obtain $CH_2Cl_2$ and 1,4-bis (difluoromethyl)tetrafluorobenzene (DFMTFB). Since 1,4-bis(difluoromethyl)tetrafluorobenzene was capable of sublimation and condensed on the condenser, the crude product was washed by using $CH_2Cl_2$ to collect 1,4-bis(difluoromethyl)tetrafluorobenzene. After $CH_2Cl_2$ was removed, 6.51 g of 1,4-bis(difluoromethyl)tetrafluorobenzene were obtained and its resultant yield was 27.2%.

The resultant product of the present example was verified to be 1,4-bis(difluoromethyl)tetrafluorobenzene through chemical analyses. The data of the chemical analyses are listed as follows.

(a) Mass spectrum analysis: M⁺ 250
(b) ¹H NMR (Tetramethylsilane, TMS):
chemical shift 6.92 ppm t, J=53.8
(c) ¹⁹F NMR (CFCl₃):
chemical shift 143.3 ppm s (aromatic F)
115.8 ppm d, J=53.8 (aliphatic F)
integration ratio (aromatic F/aliphatic F)=1/1

Examples 3 to 10

5.00 g (0.063 mole) of 1,4-bis(dichloromethyl)tetrafluorobenzene (DCMTFB), 0.50 g of tetraphenylphosphonium bromide (PTC(Br)), 8.50 g of KF, and 30 g of N,N-dimethylformamide (DMF) were added into the reacting flask. The oil bath was heated to 120° C. and stirred by a stirrer to perform the reaction for 17 hours. The product was analyzed by gas chromatography (GC) to obtain compounds 4F/2F/DCMTFB=20.7/47.2/22.1 (GC area %). The compound 4F (as formula (1)), 3F (as formula (2)), 2F (as formula (3)), 1F (as formula (4)) and DCMTFB (as formula (5)) are respectively represented by the following formulas (1) to (5).

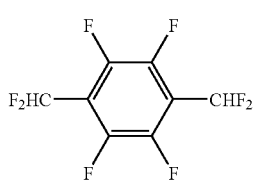

formula (1)

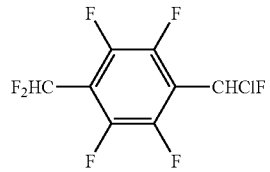

formula (2)

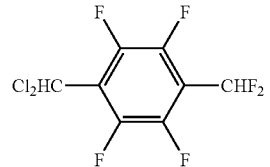

formula (3)

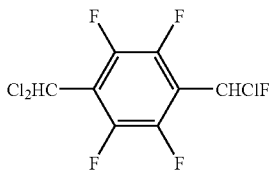

formula (4)

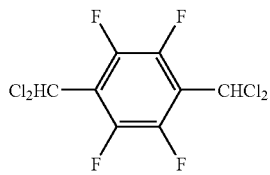

formula (5)

The methods in Examples 4 to 10 all were performed in the same manner as Example 3. The amounts of the reactants, the reaction conditions, and the GC results of Examples 3 to 10 all are shown as listed in Table 1.

Although the present invention has been explained in relation to its preferred embodiment, it is to be understood that many other possible modifications and variations can be made without departing from the scope of the invention as hereinafter claimed.

TABLE 1

| Example | DCMTFB (g) | Alkali metal flouride Kind | Alkali metal flouride Gram | Solvent Kind | Solvent Gram | Catalyst (PTC) (g) | Reaction temperature (°C.) | Reaction time (hr) | Remarks |
|---|---|---|---|---|---|---|---|---|---|
| 3 | 5.00 | KF | 8.50 | DMF | 30.00 | 0.50 (Br) | ~120 | 17.0 | GC:4F/2F/DCMTFB = 20.7/47.2/22.1 |
| 4 | 5.00 | KF | 7.80 | Sulpholane | 23.06 | 0.52 (CE15) | 80~85 90~95 | 5.5 21.33 | GC:4F/2F/DCMTFB = 0.96/38.77/35.99 |
| 5 | 10.00 | KF | 15.02 | Sulpholane | 55.75 | 1.02 (CE18) | ~120 | 23.0 | GC:4F/2F/DCMTFB = 7.39/8.89/4.55 |
| 6 | 9.36 | KF | 14.38 | Acetonitrile | 17.03 7.93 3.20 | 0.95 (Br) | 82 | 48.0 | GC:4F/2F/DCMTFB = 10.66/61.47/3.34 |
| 7 | 1.00 | KF | 5.00 | TFP | 15.00 | 0.20 (A) 0.30 (Br) | ~120 | 17.0 | GC:4F/2F/1F/DCMTFB = 0.67/8.96/12.43/53.93 |
| 8 | 1.00 | KF | 5.00 | Acetonitrile | 16.00 | 0.10 (A) 0.20 (Br) | ~85 | 42.0 | GC:4F/2F/DCMTFB = 4.00/90.00/2.00 |
| 9 | 1.00 | CsF | 3.80 | Acetonitrile | 12.00 | — | ~85 | 15.0 | GC:4F/3F/2F/DCMTFB = 0.94/3.68/4.60/87.3 |
| 10 | 1.00 | CsF · 1.5H$_2$O | 4.00 | Acetonitrile | 10.00 | 0.10 (CE18) | 85~90 | 23.0 | GC:4F/2F/DCMTFB = 0.2/2.0/96.3 |

PTC(Br): Tetraphenylphosphonium bromide
PTC(A): Tetramethylammomum chloride
CE15: 15-crown-5-ether
CE18: 18-crown-6-ether
TFP: Tetrafluoropropanol

What is claimed is:

1. A method for producing 1,4-bis(difluoromethyl)tetrafluorobenzene, comprising the following steps:
   (a) mixing 1,4-bis(dichloromethyl)tetrafluorobenzene, a catalyst, an aprotic polar solvent, and an alkali metal fluoride to form a reaction mixture;
   (b) heating the reaction mixture to perform a reaction; and
   (c) purifying the reaction mixture to obtain 1,4-bis(difluoromethyl)tetrafluorobenzene.

2. The method as claimed in claim 1, wherein the step (a) comprises the following steps:
   (a1) mixing 1,4-bis(dichloromethyl)tetrafluorobenzene, a catalyst, and an aprotic polar solvent in a reactor to form a mixture;
   (a2) heating the mixture until the 1,4-bis(dichloromethyl) tetrafluorobenzene dissolves; and
   (a3) adding an alkali metal fluoride to the mixture to form the reaction mixture.

3. The method as claimed in claim 1, wherein the reaction time of the step (b) is in the range of from 1 to 48 hours.

4. The method as claimed in claim 1, wherein the reaction temperature of the step (b) is in the range of from 40 to 160° C.

5. The method as claimed in claim 1, wherein the catalyst is at least one selected from the group consisting of quaternary ammonium salt, quaternary phosphonium salt, and crown ether.

6. The method as claimed in claim 5, wherein the quaternary ammonium salt is tetramethyl ammonium chloride.

7. The method as claimed in claim 5, wherein the quaternary phosphonium salt is tetraphenylphosphonium bromide.

8. The method as claimed in claim 5, wherein the crown ether is 18-crown-6-ether.

9. The method as claimed in claim 1, wherein the aprotic polar solvent is acetonitrile, sulpholane, or N,N-dimethylformamide.

10. The method as claimed in claim 1, wherein the alkali metal fluoride is KF or CsF.

11. The method as claimed in claim 1, wherein the mole number of the alkali metal fluoride is in the range of from 1-fold to 16-fold greater than that of 1,4-bis(dichloromethyl) tetrafluorobenzene.

12. The method as claimed in claim 1, wherein the amount of the catalyst is in the range of from 1 to 40% wt based on 1,4-bis(dichloromethyl)tetrafluorobenzene.

13. The method as claimed in claim 1, wherein purifying in the step (c) is to filtrate, extract, distil, and sublimate the reaction mixture.

* * * * *